(12) United States Patent
Xiong et al.

(10) Patent No.: US 8,802,929 B2
(45) Date of Patent: Aug. 12, 2014

(54) MIR164 GENE THAT CONTROLS PLANT ROOT SYSTEM DEVELOPMENT AND FERTILITY AND USE THEREOF

(75) Inventors: Lizhong Xiong, Wuhan (CN); Kabin Xie, Wuhan (CN); Xin Hou, Wuhan (CN)

(73) Assignee: Huazhong Agricultural University, Hubei Province (CN)

( * ) Notice: Subject to any disclaimer, the term of this patent is extended or adjusted under 35 U.S.C. 154(b) by 0 days.

(21) Appl. No.: 13/319,534

(22) PCT Filed: May 12, 2010

(86) PCT No.: PCT/CN2010/000677
§ 371 (c)(1),
(2), (4) Date: Jan. 3, 2012

(87) PCT Pub. No.: WO2010/130155
PCT Pub. Date: Nov. 18, 2010

(65) Prior Publication Data
US 2012/0102598 A1    Apr. 26, 2012

(30) Foreign Application Priority Data

May 13, 2009    (CN) .......................... 2009 1 0062045

(51) Int. Cl.
*A01H 5/00*    (2006.01)
*C12N 15/82*    (2006.01)
*C12N 15/113*    (2010.01)

(52) U.S. Cl.
USPC ........ 800/290; 800/285; 800/320.2; 800/287; 435/468; 536/24.5

(58) Field of Classification Search
None
See application file for complete search history.

(56) References Cited

U.S. PATENT DOCUMENTS

2006/0123505 A1*    6/2006   Kikuchi et al. ............... 800/278

FOREIGN PATENT DOCUMENTS

CN    101544987    9/2009

OTHER PUBLICATIONS

Gou et al (The Plant Cell, vol. 17, 1376-1386, May 2005).*
Kabin (Chinese Doctoral Dissertations, Dec. 18, 2008—cited in Applicant's IDS).*
Kabin, Xie, "Full Length cDNA Library Construction and Functional Analysis of Two Micrornas in Rice", Chinese Doctoral Dissertations, Dec. 18, 2008, English translation of first 5 pages and full text in Chinese.
Peaucelle et al, "Plants expressing a miR164-resistant CUC2 gene reveal the importance of post-meristematic maintenance of phyllotaxy in Arabidopsis", Development, 2007, pp. 1045-1050, vol. 134 No. 6.
Raman et al., "Interplay of miR164, Cup-Shaped Cotyledon genes and Lateral Suppressor controls axillary meristem formation in *Arabidopsis thaliana*", The Plant Journal, 2008, pp. 65-76, vol. 55.
Reinhart et al., "MicroRNAs in plants", Genes and Development, 2002, pp. 1616-1626, vol. 16.
Guo et al., "MicroRNA Directs mRNA Cleavage of the Transcription Factor NAC1 to Downregulate Auxin Signals for Arabidopsis Lateral Root Development", The Plant Cell, May 2005, pp. 1376-1386, vol. 17.

* cited by examiner

*Primary Examiner* — Medina A Ibrahim
*Assistant Examiner* — Lee A Visone
(74) *Attorney, Agent, or Firm* — Thompson Coburn LLP; J. Wendy Davis

(57) ABSTRACT

A rice microRNA, miR164 gene, that controls plant root system development and fertility, is obtained through gene isolation, cloning and function verification. Uses of a nucleic acid fragment comprising miR164, which fragment may confer a transformed plant with the ability to increase root number and to alter fertility, wherein the said nucleic acid fragment is selected from one of the following nucleotide sequences: 1) a DNA sequence as shown in SEQ ID NO: 1; 2) a RNA sequence as shown in SEQ ID NO:2; or 3) the conserved sequence of miR164 having the same function as 1) or 2). The nucleotide sequence containing the precursor of miR164 is ligated with an exogenous promoter and introduced into rice to obtain transgenic rice plants which has large root systems but became infertile. The fertility can be restored by external application of phytohormones.

3 Claims, 4 Drawing Sheets

US 8,802,929 B2

MIR164 GENE THAT CONTROLS PLANT ROOT SYSTEM DEVELOPMENT AND FERTILITY AND USE THEREOF

CROSS-REFERENCE TO RELATED APPLICATIONS

This application is National Stage application of International Patent Application No. PCT/CN2010/000677, filed May 12, 2010 and incorporated herein by reference in its entirety, which claims the benefit of Chinese Patent Application No. 200910062045.0 filed May 13, 2009 and incorporated herein by reference in its entirety.

INCORPORATION OF SEQUENCE LISTING

A sequence listing is contained in the file named "58860_seq.txt" which is 2,190 bytes (measured in MS-Windows) and was created on Nov. 8, 2011. The electronic sequence listing was previously filed on Nov. 9, 2011 and is incorporated herein by reference.

TECHNICAL FIELD

The present disclosure pertains to the field of plant genetic engineering. Specifically, the present disclosure relates to a microRNA (miRNA) or precursor thereof that influences plant root system development and fertility, which was obtained through gene isolation, cloning and function verification. The present disclosure also relates to use of the microRNA (miRNA) or precursor thereof in rice genetic improvement. Said miRNA is capable of regulating the development and growth of plant root system and the fertility of flower organ. When the precursor of the miRNA was linked to an ubiquitin promoter followed by introduction into rice, the transgenic rice plants obtained showed a significantly enhanced development of root system, but became infertile; yet the fertility of the transgenic plants might be partially restored by external application of hormones. This technology could be used to breed a sterile line or maintainer line with a large root system, thereby facilitating the breeding of hybrid rice.

BACKGROUND ART miRNAs are small RNA molecules with a length of 20-22 nt (nucleotide), present in eukaryotes and encoded by the genomes of the eukaryotes. MiRNAs recognize target genes mainly by complementarily pairing with the RNA of target genes and then inhibit the expression of the target genes through miRNA-RISC (RNA induced silence complex) (Jones-Rhoades M W, Bartel D P, and Bartel B. MicroRNAs and their regulatory roles in plants. *Annual Review of Plant Biology,* 2006, 57: 19-53). Each miRNA gene produces at least three small RNA species, including a long primary miRNA transcript (pri-miRNA), an intermediate ~60 nt precursor miRNA (pre-miRNA), and a ~21 nt mature miRNA, through sequential endonucleolytic maturation steps (Kim VN MicroRNA biogenesis: coordinated cropping and dicing. *Nat Rev Mol Cell Biol* 2005, 6: 376-385). The transcripts of miRNA genes (pre-miRNAs) are structurally consistent with common mRNAs, having such structures as 5'-CAP and 3' poly(A). Therefore pre-miRNAs can also be cloned from conventional cDNA library. Common miRNAs have no protein-encoding region in their transcripts. While pre-miRNA molecules may have several very small ORFs, no pre-miRNA molecules from which a protein can be translated have been found. Pre-miRNAs from which miRNAs are formed are located in the transcripts of miRNA genes, and they have a length of 60 nt to 200 nt, or more than 200 nt for some of them. Pre-miRNAs can form a stable foldback secondary structure that is recognized by an enzyme necessary for miRNA maturation. MiRNAs play very important regulatory roles during development and growth of a plant, involving in various aspects of plant development, growth, and biological and non-biological stresses. The target genes of many miRNAs belong to transcription factor family. The same miRNA may often inhibit the functions of a variety of target genes, while regulating various interconnected processes during plant development and growth. For example, overexpression of miR156 increases the number of leaves of *Arabidopsis thaliana* more than 100 times and plant dry weight 5 times, and delays flowering time (Wu G and Poethig R S. Temporal regulation of shoot development in *Arabidopsis thaliana* by miR156 and its target *SPL3*. *Development,* 2006, 133: 3539-3547). In corn, miR172 regulates the sex differentiation of flower organ in addition to flowering time (Chuck G, Meeley R, Irish E, Sakai H, and Hake S. The maize tasselseed4 microRNA controls sex determination and meristem cell fate by targeting *Tasselseed6/indeterminate spikelet1*. *Nat Genet,* 2007, 39: 1517-1521). MiR159 has an important regulatory role in ABA response, seed germination, flower development and leaf shape, etc. Overexpresion of miR159 in plants will result in the plant's reduced sensitivity to abscisic acid (ABA) during the germination period, delayed flowering time and decreased anther fertility (Reyes J L and Chua N H. ABA induction of miR159 controls transcript levels of two MYB factors during Arabidopsis seed germination. *Plant J,* 2007, 49: 592-606).

Rice is the most important cereal crop. Altering the morphology, fertility and flowering time of rice plants is of great significance for increasing rice yield. MiRNAs are a key regulatory factor during plant development and growth. They generally can alter many key traits of plants, especially for those highly conserved miRNAs. The development of plant root system is critical for the plant to absorb nutrients and water. A plant with a large root system will have increased absorption of nutrients and water and enhanced resistance to stresses. On the other hand, controlling plant fertility will be of great significance and usefulness for breeding hybrid crop varieties by virtue of heterosis.

DISCLOSURE OF THE INVENTION

It is an object of the present disclosure to isolate and clone from rice a DNA fragment comprising a sequence of a miRNA gene. It is another object of the present disclosure to use the miRNA molecule produced from said miRNA gene to control the root number and the fertility of rice. Analysis reveals that this miRNA molecule is identical to plant miRNA164, hence the DNA fragment is designated as miR164 gene.

The present disclosure relates to use of a nucleic acid fragment comprising miR164, which fragment may confer a transformed plant with the ability to increase root number and to alter fertility, wherein said nucleic acid fragment is selected from one of the following nucleotide sequences:
1) a DNA sequence as shown in SEQ ID NO: 1 in the Sequence Listing;
2) a RNA sequence as shown in SEQ ID NO: 2 in the Sequence Listing; or
3) the conserved sequence of miR164 having the same function as 1) or 2), which conserved sequence forms a mature microRNA having a sequence similarity of more than 90% the sequence of the mature microRNA formed by 1) or 2).

In a preferable embodiment, the nucleic acid is used for promoting the growth of rice root system. In another preferable embodiment, the nucleic acid is used for breeding rice sterile lines and maintainer lines as well as hybrid rice.

As miRNAs serve to inhibit the function of their target genes by complementary pairing with the RNA molecules of the target genes by virtue of small mature RNA molecules with a length of 20 to 22 nt, and the sequence of mature miR164 is highly conserved in plants, miR164 sequence isolated from plants other than rice, or functionally conserved miR164 sequence artificially synthesized may give the same or essentially the same result as described in the present disclosure.

A cloned miR164 may be used as a probe to screen cDNA or genomic libraries for the gene according to the present disclosure or a homologue thereof. Alternatively, PCR (polymerase chain reaction) may be used to amplify from genome, mRNAs and cDNAs the miR164 gene according to the present disclosure or any DNA fragment or a homologue thereof of interest. By using the above technology, a sequence comprising miR164 gene can be isolated, ligated with any vector capable of directing the expression of an endogenous gene in a plant to transform the plant, to obtain transgenic plants with increased root number and altered fertility. When the gene according to the present disclosure is ligated into a plant expression vector, any strong promoter or inducible promoter can be placed in front of its transcription initiation site.

The expression vector carrying the miR164 gene according to the present disclosure can be introduced into plant cells using conventional biotechnological methods, such as using Ti plasmid, plant viral vector, direct DNA transformation, microinjection, electroporation, etc. (Weissbach, 1998, Method for Plant Molecular Biology VIII, Academy Press, New York, pp. 411-463; Geiserson and Corey, 1998, Plant Molecular Biology ($2^{nd}$ Edition)).

Hosts that can be transformed with the expression vector comprising the miR164 gene according to the present disclosure include a variety of plants, including rice. These plants can be bred into infertile varieties with large root systems, whose fertility can be restored by external application of hormones.

The invention also relates to a recombinant DNA construct comprising DNA from a ubiquitin promoter that is functional in a plant cell and is operably linked to a DNA that is transcribed to produce a microRNA molecule having the RNA nucleotide sequence of SEQ ID NO: 2. In a preferable embodiment, said DNA that is transcribed to produce a microRNA has a polynucleotide sequence of SEQ ID NO: 1.

An embodiment of the invention provides a transgenic plant cell comprising the recombinant DNA construct as described above.

A further embodiment of the invention provides a method of enhancing the root system in a plant by expressing in a plant microRNA molecules with SEQ ID NO: 2. In one preferable embodiment, said plant is selected from the group consisting of corn, soybean, cotton, canola, alfalfa, wheat, rice, sugarcane and sugar beet plant. In another preferable embodiment, said microRNA molecules are produced from a recombinant DNA construct comprising a promoter operably linked to DNA with a polynucleotide sequence of SEQ ID NO: 1. In a further preferable embodiment, said promoter is the ubiquitin promoter.

The present invention is further illustrated by the examples below with reference to accompanying drawings.

BRIEF DESCRIPTION OF THE DRAWINGS

SEQ ID NO: 1 in the Sequence Listing shows the DNA sequence for miR164 gene isolated and cloned according to the present disclosure which, when expressed in a plant, produces mature microRNA molecules. Positions 1-21 and 868-887 represent the primer sequences for amplifying miR164 gene, and positions 43-63 in capital letters represents the DNA sequence to which SEQ ID NO: 2 corresponds.

SEQ ID NO: 2 in the Sequence Listing shows the mature microRNA sequence formed from expression of the miR164 gene, which corresponds to the DNA sequence of positions 43-63 in SEQ ID NO: 1.

FIGS. 6A to 6E show the morphology of spikelets (in each figure, the left panel shows the transgenic plant overexpressing miR164, and the right panel shows the wild-type control). FIGS. 6F to 6K show the morphology of stamens and anther sacs (FIGS. 6F to 6H show the transgenic plants overexpressing miR164, and FIGS. 6I to 6K show the wild-type control); FIGS. 6L to 6O show the morphology of pollen and fertility (FIGS. 6L to 6M show the transgenic plants overexpressing miR164, and FIGS. 6N to 6O show the wild-type control).

EXAMPLES

The following examples illustrate the present invention, describing the method of isolating and cloning the DNA fragments for miR164 and its precursor pre-miR164, as well as the method of verifying their function. In light of the following description and these examples, the basic features of the present disclosure will occur to those skilled in the art, and various changes and modifications to the present disclosure can be made to adapt for various uses and conditions without departing from the spirit and scope of the present disclosure.

Example 1

Isolation and Cloning of the Precursor of miR164—pre-miR164

Total RNA was extracted from leaves of the rice variety "Nipponbare" (a published rice variety) using TRIZOL reagent (Invitrogen Corp.) according to the manufacturer's instruction, and then reverse transcribed into cDNAs with reverse transcriptase SSII (purchased from Invitrogen Corp.) under the following conditions: 65° C. for 5 min, 42° C. for 120 min, and 70° C. for 10 min. Primers containing restriction sites, GPF (5'-GGTACCAATGGTACCTGGCGACACA-GAGAGAGA-3', SEQ ID NO:3, a sequence-specific primer plus KpnI site) and GPR (5'-GGATCCAATGGATC-CCGAACTGAGCTGGAGAGACA-3', SEQ ID NO:4, a sequence-specific primer plus BamHI site), were used to amplify the cDNA of pre-miR164 (899 bp). PCR reaction was performed under the following conditions: predenaturing at 94° C. for 3 min; 35 cycles of 94° C. for 30 sec, 53° C. for 30 sec, and 72° C. for 1 min; and extension at 72° C. for 10 min. The amplified PCR products were ligated into pGEM-T vector (Promega Co., Ltd). The desired cDNA of the gene was obtained by screening for a positive clone and sequencing. The positive clone obtained was designated as pGEM-pre-miR164.

Example 2

Construction and Genetic Transformation of Pre-miR164 Overexpression Vector

In order to better analyze the function of miR164, its precursor, pre-miR164, was overexpressed in rice to study its function by observing the phenotypes of transgenic plants.

Figure 1:
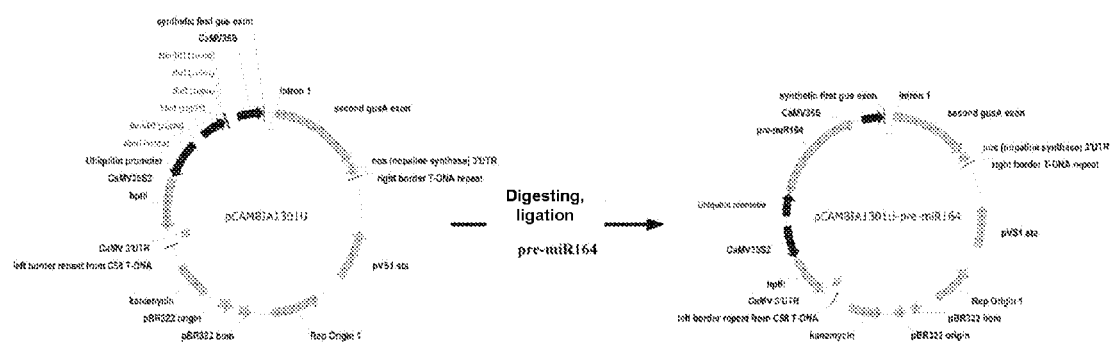
FIG. 1. The schematic diagram for constructing an overexpression vector according to the present disclosure. Pre-miR164 gene is subjected to restriction digestion and inserted downstream of a ubiquitin promoter.

The overexpression vector was constructed as follows. The plasmid from the positive clone pGEM-pre-miR164 obtained in Example 1 was digested with both BamHI and KpnI, and the insert was recovered. The genetic transformation vector pCAMBIA1301U carrying ubiquitin promoter was digested with BamHI and KpnI. The genetic transformation vector pCAMBIA1301U was obtained based on the plant genetic transformation vector pCAMBIA1301 (available from CAMBIA (Center for the Application of Molecular Biology to International Agriculture), Australia) extensively used in the world by incorporating a widely-used ubiquitin promoter which directs constitutive expression at the restriction site for EcoRI and SacI (See: Toki S, Takamatsu S, Nojiri C, Ooba S, Anzai H, Iwata M, Christensen A H, Quail P H, and Uchimiya H. Expression of a Maize Ubiquitin Gene Promoter-bar Chimeric Gene in Transgenic Rice Plants. *Plant Physiol*, 1992, 100: 1503-1507), as shown in FIG. 1. After digestion, the digested product was purified by extraction with chloroform: isoamyl alcohol (24:1 v/v). The fragment containing pre-miR164 was ligated with the digested vector, and transformed into *E. coli* DH 10β strain (Invitrogen). The transformation vector was obtained by means of screening for a positive clone by restriction digestion.

The transformation vector was introduced into the rice variety "Zhonghua 11" (a publicly used rice variety, available from China National Rice Research Institute) using rice genetic transformation system mediated by *Agrobacterium*. Transgenic plants were obtained through pre-cultivation, infection, co-cultivation, screening of the calli with hygromycin resistance, differentiation, rooting, hardening of seedling and transplantation. The rice (japonica rice subspecies) genetic transformation system mediated by *Agrobacterium* was modified on the basis of the method reported by Hiei, et al. (See Hiei, et al., Efficient transformation of rice, *Oryza sativa* L., mediated by *Agrobacterium* and sequence analysis of the boundaries of the T-DNA, *Plant Journal* 6:271-282, 1994). A total of 40 independent transgenic rice plants were obtained using the transformation vector.

The procedure was carried out as follows: (1) Callus Induction: Mature rice seeds were husked, and then were successively treated with 70% alcohol for 1 minute and surface-disinfected with 0.15% $HgCl_2$ for 15 minutes. The seeds were rinsed with sterilized water for 4-5 times. The treated seeds were put onto the induction medium (the formulation thereof is as described below). The seeded medium was placed in darkness for 4-week culture at 25±1° C. (2) Subculture: Bright yellow, compact and relatively dry embryogenic calli were selected, put onto subculture medium as described below, and cultured in darkness for 2 weeks at 25±1° C. (3) Pre-culture: The compact and relatively dry embryogenic calli were selected, put onto the pre-culture medium as described below, and cultured in darkness for 2 weeks at 25±1° C. (4) *Agrobacterium* Culture: *Agrobacterium* EHA 105 (a commercial strain, available from CAMBIA) was pre-cultured on the LA medium with corresponding resistance selection at 28° C. for 2 days. Then the *Agrobacterium* was transferred to the suspension medium as described below and cultured on a shaker at 28° C. for 2-3 hours. (5) *Agrobacterium* Infection: The pre-cultured calli were transferred into a sterilized glass bottle. The *Agrobacterium* suspension was adjusted to $OD_{600}$ 0.8-1.0. The calli were immersed in the *Agrobacterium* suspension for 30 minutes and then transferred onto a sterilized filter paper and dried. The dried calli were put onto the co-culture medium as described below for 3-day culture at 19-20° C. (6) Washing and Selective Culture of Calli: The calli were washed with sterilized water until no *Agrobacterium* was observed. The washed calli were immersed in sterilized water containing 400 ppm carbenicillin (CN) for 30 minutes and then transferred onto a sterilized filter paper and dried. The dried calli were transferred onto the selective medium as described below and screened for 2-3 times, 2 weeks for each time (the concentration of carbenicillin was 400 ppm for the first screen and 250 ppm for later screens, and the concentration of hygromycin was 250 ppm). (7) Differentiation: The resistant calli obtained were transferred to the pre-differentiation medium as described below, and cultured in darkness for 5-7 weeks. The pre-differentiated calli were transferred to the differentiation medium as described below, and cultured under light at 26° C. (8) Rooting: The roots of the plantlets generated during differentiation were cut off. Then the plantlets were transferred to the rooting medium as described below, and cultured under light at 26° C. for 2-3 weeks. (9) Transplantation: The residual medium on the roots of the plantlets was washed off, and those plantlets with good root system were transferred into a greenhouse. The greenhouse was maintained moisturized in the first few days of transplantation.

Formulation of the Reagents:
(1) Abbreviations for Reagents and Solutions

The abbreviations for phytohormones used in the media of the present disclosure are as follows: 6-BA (6-Benzylaminopurine); CN (Carbenicillin); KT (Kinetin); NAA (Naphthaleneacetic acid); IAA (Indole-3-acetic acid); 2,4-D (2,4-Dichlorophenoxyacetic acid); AS (Acetosyringone); CH (Casein Hydrolysate); HN (Hygromycin B); DMSO (Dimethyl Sulfoxide); N6mac (macroelement solution for N6 basal medium); N6mic (microelement solution for N6 basal medium); MSmac (macroelement solution for MS basal medium); and MSmic (microelement solution for MS basal medium).

(2) Formulations of Primary Solutions:

1) Preparation of Macroelement Mother Solution for N6 Basal Medium (10× Concentrate):

| | |
|---|---|
| Potassium nitrate ($KNO_3$) | 28.3 g |
| Potassium dihydrogen phosphate ($KH_2PO_4$) | 4.0 g |
| Ammonium sulfate (($NH_4)_2SO_4$) | 4.63 g |
| Magnesium sulfate ($MgSO_4 \cdot 7H_2O$) | 1.85 g |
| Potassium chloride ($CaCl_2 \cdot 2H_2O$) | 1.66 g |

These compounds were dissolved in succession with distilled water and then the volume was brought to 1000 ml with distilled water at room temperature.

2) Preparation of Microelement Mother Solution for N6 Basal Medium (100× Concentrate):

| | |
|---|---|
| Potassium iodide (KI) | 0.08 g |
| Boric acid ($H_3BO_3$) | 0.16 g |
| Manganese sulfate ($MnSO_4 \cdot 4H_2O$) | 0.44 g |
| Zinc sulfate ($ZnSO_4 \cdot 7H_2O$) | 0.15 g |

These compounds were dissolved in distilled water and then the volume was brought to 1000 ml with distilled water at room temperature.

3) Preparation of Iron Salt ($Fe_2EDTA$) Stock Solution (100× Concentrate):

800 ml double-distilled water was prepared and heated to 70° C., then 3.73 g $Na_2EDTA.2H_2O$ was added and dissolved thoroughly. The resulting solution was kept in 70° C. water bath for 2 h, then brought to 1000 ml with distilled water and stored at 4° C. until use.

4) Preparation of Vitamin Stock Solution (100× Concentrate):

| | |
|---|---|
| Nicotinic acid | 0.1 g |
| Vitamin B1 (Thiamine HCl) | 0.1 g |
| Vitamin B6 (Pyridoxine HCl) | 0.1 g |
| Glycine | 0.2 g |
| Inositol | 10 g |

Distilled water was added to dissolve the compounds. The resulting solution was brought to 1000 ml with distilled water and stored at 4° C. until use.

5) Preparation of Macroelement Mother Solution for MS Basal Medium (10× Concentrate):

| | |
|---|---|
| Ammonium nitrate ($NH_4NO_3$) | 16.5 g |
| Potassium nitrate | 19.0 g |
| Potassium dihydrogen phosphate | 1.7 g |
| Magnesium sulfate | 3.7 g |
| Calcium chloride | 4.4 g |

These compounds were dissolved in distilled water and then the volume was brought to 1000 ml with distilled water at room temperature.

6) Preparation of Microelement Mother Solution for MS Basal Medium (100× Concentrate):

| | |
|---|---|
| Potassium iodide | 0.083 g |
| Boric acid | 0.62 g |
| Manganese sulfate | 0.86 g |
| Sodium molybdate ($Na_2MoO_4 \cdot 2H_2O$) | 0.025 g |
| Copper sulphate ($CuSO_4 \cdot 5H_2O$) | 0.0025 g |

These compounds were dissolved in distilled water and then the volume was brought to 1000 ml with distilled water at room temperature.

7) 2,4-D Stock Solution, 6-BA Stock Solution, Naphthaleneacetic Acid (NAA) Stock Solution, Indoleacetic Acid (IAA) Stock Solution were all 1 mg/ml.

8) Glucose Stock Solution was 0.5 g/ml.

9) Preparation of AS Stock Solution: 0.392 g AS was Weighed and Dissolved in 10 ml DMSO.

(3) Formulation of Media for Genetic Transformation of Rice

1) Induction Medium:

| | |
|---|---|
| N6mac mother solution (10X) | 100 ml |
| N6mic mother solution (100X) | 10 ml |
| $Fe^{2+}$ EDTA stock solution (100X) | 10 ml |
| Vitamin stock solution (100X) | 10 ml |
| 2,4-D stock solution | 2.5 ml |
| Proline | 0.3 g |
| CH | 0.6 g |
| Sucrose | 30 g |
| Phytagel | 3 g |

Distilled water was added to a volume of 900 ml, and the pH value was adjusted to 5.9 with 1 N potassium hydroxide. The resulting mixture was boiled and brought to 1000 ml. The resulting medium was dispensed into 50 ml Erlenmeyer flasks (25 ml/flask), and the flasks were sealed and sterilized.

2) Subculture Medium:

| | |
|---|---|
| N6mac mother solution (10X) | 100 ml |
| N6mic mother solution (100X) | 10 ml |
| $Fe^{2+}$ EDTA stock solution (100X) | 10 ml |
| Vitamin stock solution (100X) | 10 ml |
| 2,4-D stock solution | 2.0 ml |
| Proline | 0.5 g |
| CH | 0.6 g |
| Sucrose | 30 g |
| Phytagel | 3 g |

Distilled water was added to a volume of 900 ml, and the pH value was adjusted to 5.9 with 1 N potassium hydroxide. The resulting mixture was boiled and brought to 1000 ml. The resulting medium was dispensed into 50 ml Erlenmeyer flasks (25 ml/flask), and the flasks were sealed and sterilized.

3) Pre-Culture Medium:

| | |
|---|---|
| N6mac mother solution (10X) | 12.5 ml |
| N6mic mother solution (100X) | 1.25 ml |
| $Fe^{2+}$ EDTA stock solution (100X) | 2.5 ml |
| Vitamin stock solution (100X) | 2.5 ml |
| 2,4-D stock solution | 0.75 ml |
| CH | 0.15 g |
| Sucrose | 5 g |
| Agarose | 1.75 g |

Distilled water was added to a volume of 250 ml, and the pH value was adjusted to 5.6 with 1 N potassium hydroxide. The resulting medium was sealed and sterilized. Prior to use, the medium was melted under heat and 5 ml glucose stock solution and 250 μl AS stock solution were added. The resulting medium was dispensed into Petri dishes (25 ml/dish).

4) Co-Culture Medium:

| | |
|---|---|
| N6mac mother solution (10X) | 12.5 ml |
| N6mic mother solution (100X) | 1.25 ml |
| $Fe^{2+}$ EDTA stock solution (100X) | 2.5 ml |
| Vitamin stock solution (100X) | 2.5 ml |
| 2,4-D stock solution | 0.75 ml |
| CH | 0.2 g |
| Sucrose | 5 g |
| Agarose | 1.75 g |

Distilled water was added to a volume of 250 ml, and the pH value was adjusted to 5.6 with 1 N potassium hydroxide. The resulting medium was sealed and sterilized. Prior to use, the medium was melted under heat, and 5 ml glucose stock solution and 250 μl AS stock solution were added. The resulting medium was dispensed into Petri dishes (25 ml/dish).

5) Suspension Medium:

| | |
|---|---|
| N6mac mother solution (10X) | 5 ml |
| N6mic mother solution (100X) | 0.5 ml |
| $Fe^{2+}$ EDTA stock solution (100X) | 0.5 ml |
| Vitamin stock solution (100X) | 1 ml |
| 2,4-D stock solution | 0.2 ml |
| CH | 0.08 g |
| Sucrose | 2 g |

Distilled water was added to a volume of 100 ml, and the pH value was adjusted to 5.4. The resulting medium was dispensed into two 100 ml Erlenmeyer flasks and the flasks were sealed and sterilized. Prior to use, 1 ml glucose stock solution and 100 μl AS stock solution were added.

6) Selective Medium:

| | |
|---|---|
| N6mac mother solution (10X) | 25 ml |
| N6mic mother solution (100X) | 2.5 ml |
| $Fe^{2+}$ EDTA stock solution (100X) | 2.5 ml |
| Vitamin stock solution (100X) | 2.5 ml |
| 2,4-D stock solution | 0.625 ml |
| CH | 0.15 g |
| Sucrose | 7.5 g |
| Agarose | 1.75 g |

Distilled water was added to a volume of 250 ml, and the pH value was adjusted to 6.0. The resulting medium was sealed and sterilized. Prior to use, the medium was melted and 250 μl HN and 400 ppm CN were added. The resulting medium was dispensed into Petri dishes (25 ml/dish).

7) Pre-Differentiation Medium:

| | |
|---|---|
| N6mac mother solution (10X) | 25 ml |
| N6mic mother solution (100X) | 2.5 ml |
| $Fe^{2+}$ EDTA stock solution (100X) | 2.5 ml |
| Vitamin stock solution (100X) | 2.5 ml |
| 6-BA stock solution | 0.5 ml |
| KT stock solution | 0.5 ml |
| NAA stock solution | 50 μl |
| IAA stock solution | 50 μl |
| CH | 0.15 g |
| Sucrose | 7.5 g |
| Agarose | 1.75 g |

Distilled water was added to a volume of 250 ml, and the pH value was adjusted to 5.9 with 1N potassium hydroxide. The resulting medium was sealed and sterilized. Prior to use, the medium was melted and 250 μl HN and 200 ppm CN were added. The resulting medium was dispensed into Petri dishes (25 ml/dish).

8) Differentiation Medium:

| | |
|---|---|
| N6mac mother solution (10X) | 100 ml |
| N6mic mother solution (100X) | 10 ml |
| $Fe^{2+}$ EDTA stock solution (100X) | 10 ml |
| Vitamin stock solution (100X) | 10 ml |
| 6-BA stock solution | 2 ml |
| KT stock solution | 2 ml |
| NAA stock solution | 0.2 ml |
| IAA stock solution | 0.2 ml |
| CH | 1 g |
| Sucrose | 30 g |
| Phytagel | 3 g |

Distilled water was added to a volume of 900 ml, and the pH value was adjusted to 6.0 with 1N potassium hydroxide. The resulting mixture was boiled and brought to 1000 ml. The resulting medium was dispensed into 50 ml Erlenmeyer flasks (50 ml/flask), and the flasks were sealed and sterilized.

9) Rooting Medium:

| | |
|---|---|
| MSmac mother solution (10X) | 50 ml |
| MSmic mother solution (100X) | 5 ml |
| $Fe^{2+}$ EDTA stock solution (100X) | 5 ml |
| Vitamin stock solution (100X) | 5 ml |
| Sucrose | 30 g |
| Phytagel | 3 g |

Distilled water was added to a volume of 900 ml, and the pH value was adjusted to 5.8 with 1N potassium hydroxide. The resulting mixture was boiled and brought to 1000 ml. The resulting medium was dispensed into the rooting tubes (25 ml/tube), and the tubes were sealed and sterilized.

Example 3

Determination of the Expression Level of Rice Endogenous miR164

Figure 2:
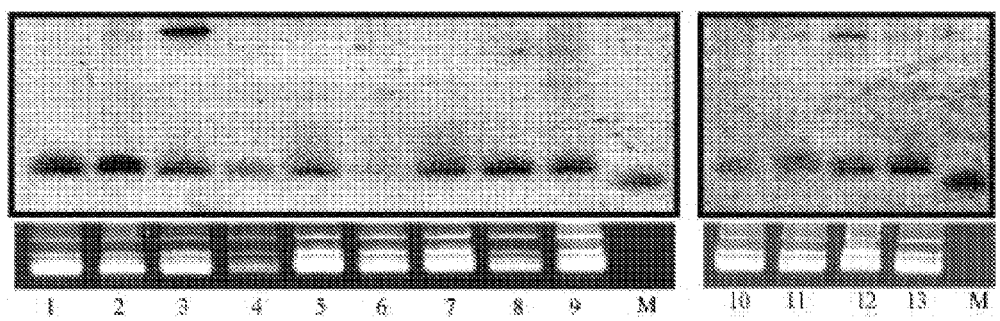
FIG. 2. The levels of expression of mature miR164 in thirteen various tissues of rice, as determined by Northern blotting: 1), root at tillering stage; 2), stem at jointing stage; 3), 4), leaf sheath at 4-leaf stage; 5), spike shorter than 0.5 cm; 6), spike of 0.5 to 1 cm; 7), spike of 3 to 5 cm; 8), spike longer than 10 cm; 9), stamen; 10), pistil; 11), shoot at 1 d after germination; 12), 3-week-old shoot; 13), 3-week-old etiolated shoot.

Total RNA was extracted from thirteen tissues collected at different growth stages of the rice variety "Minghui 63" (*Oryza sativa* L. ssp. Indica, a rice variety popularized in China) to determine the expression level of mature miR164 by Northern blotting. The thirteen tissues collected were: 1), root at tillering stage; 2), stem at jointing stage; 3) and 4), leaf sheaths at 4-leaf stage; 5), spike shorter than 0.5 cm; 6), spike of 0.5 to 1 cm; 7), spike of 3 to 5 cm; 8), spike longer than 10 cm; 9), stamen; 10), pistil; 11), shoot at 1 day after germination; 12), 3-week-old shoot; 13), 3-week-old etiolated shoot. Total RNA was extracted with TRIZOL reagent (Invitrogen Corp.) according to the manufacturer's instruction. The RNA was transferred to a membrane as described by Xie et al. (Xie K, Wu C, and Xiong L. Genomic organization, differential expression, and interaction of SQUAMOSA promoter-binding-like transcription factors and microRNA156 in rice. *Plant Physiol*, 2006, 142: 280-293). Northern hybridization was performed using miR164 as the probe. Results showed that miR164 was expressed in all the tissues collected, with a relatively low level in young panicles (see FIG. 2).

Figure 3:
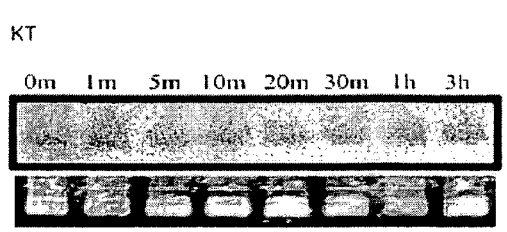
FIG. 3. The changes in the levels of expression of mature miR164 after treatment with hormones, as determined by Northern blotting. KT (kinetin, FIG. 3a); NAA, (naphthaleneacetic acid, an auxin analog, FIG. 3b); GA (gibberellin, FIG. 3c); and BR (brassinolide, FIG. 3d).
Figure 3:
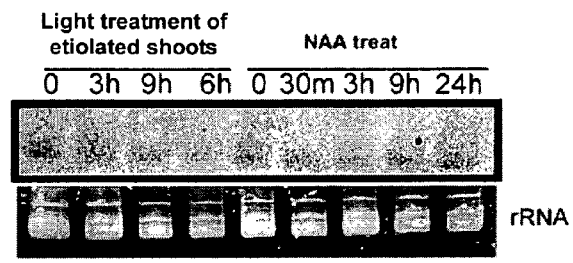
Figure 3:
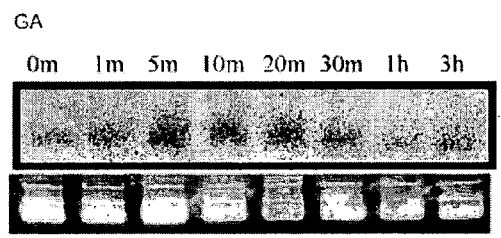
Figure 3:
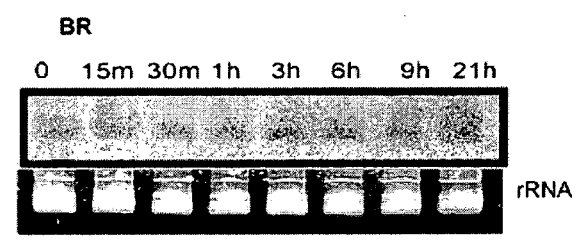

The indica rice variety "Minghui 63" was used for expression profile analysis. Phytohormone treatment was carried out by evenly spraying the hormones onto the surfaces of the rice plants at the 4-leaf stage obtained from seeds which had been induced to germinate and cultivated under normal growth conditions for 18-20 days. The plants treated with kinetin and gibberellin were sampled before treatment as well as 1 min, 5 min, 10 min, 20 min, 30 min, 1 h, and 3 h after treatment. The plants treated with naphthaleneacetic acid were sampled before treatment as well as 30 min, 3 h, 9 h and 24 h after treatment. The plants treated with brassinolide were sampled before treatment as well as 15 min, 30 min, 1 h, 3 h, 6 h, 9 h and 21 h after treatment. Light treatment of etiolated shoots was performed by subjecting seeds to induction of germination and continuous cultivation in dark for 14 days followed by transferring the etiolated shoots to normal lighting conditions. Samples were taken before light treatment as well as 3 h, 6 h and 9 h after light treatment. Total RNA was extracted from leaves using Trizol reagent (Invitrogen Corp.), and then transferred to membrane as described by Xie et al. (Xie K, Wu C, and Xiong L. Genomic organization, differential expression, and interaction of SQUAMOSA promoter-binding-like transcription factors and microRNA156 in rice. *Plant Physiol,* 2006, 142: 280-293). Northern hybridization was performed using miR164 as the probe. Results showed that the expression of miR164 was mildly increased or decreased after phytohormone treatment, decreased gradually after Kinetin (KT) treatment, and increased after gibberellin (GA) treatment, to a peak at 10 minutes after treatment, then dropping to the level before treatment. Rice shoots grown in dark had a relatively high level of expression of miR164, but the level returned to normal after light treatment. The expression level of miR164 increased 24 hours after naphthaleneacetic acid (NAA) treatment. However, there was no obvious change in the level after brassinolide (BR) treatment (FIG. 3).

Example 4

Transgenic Plants Overexpressing miR164 had Large Root Systems

Figure 4:
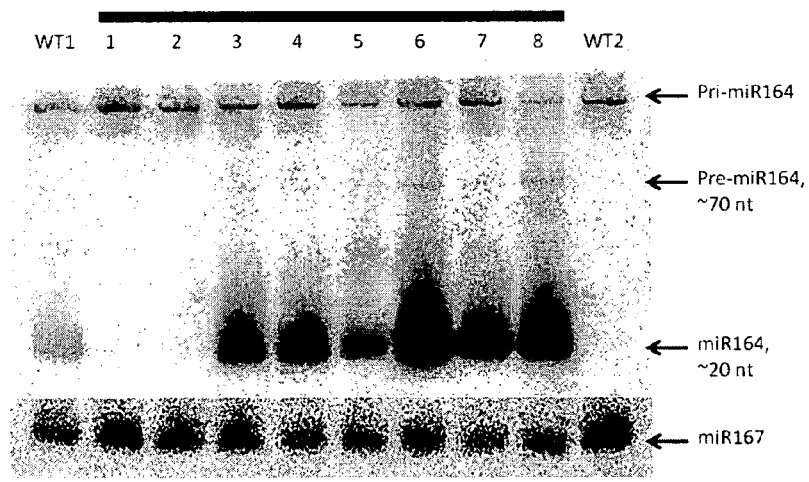
FIG. 4. Overexpression of miR164 in mature flag leaves in the transgenic rice lines, as determined by Northern blotting. WT1—young leaf of the wild type; WT2—flag leaf of the wild type.
Figure 5:
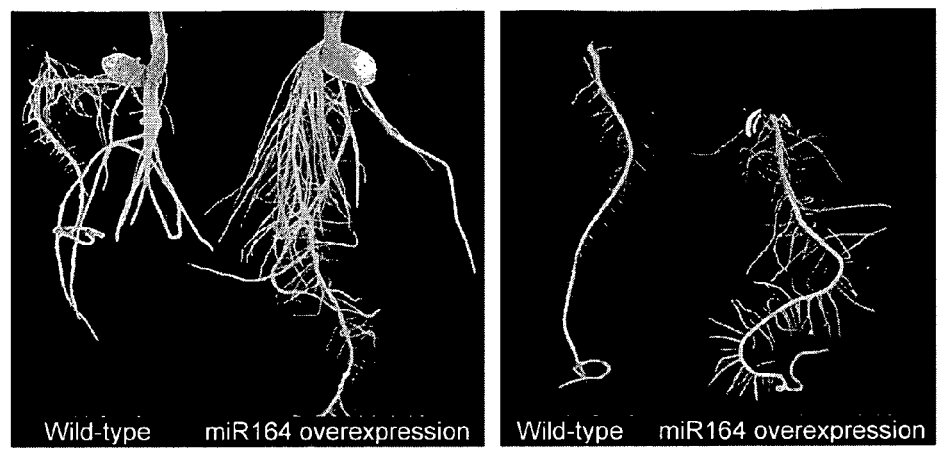
FIG. 5 shows that the transgenic plant overexpressing miR164 has a larger root system than the wild-type plant. The left panel shows the whole root system and the right panel shows the lateral roots on an individual root.

In this example, transgenic plants overexpressing miR164 (FIG. 4) and wild-type plants were grown in ½ MS medium and observed for their phenotypes. The procedure was carried out as follows, Rice seeds from transgenic lines overexpressing miR164 were husked and disinfected (75% alcohol treatment for 3 minutes followed by 0.15% $HgCl_2$ treatment for 30 minutes, and rinsed with sterile water for several times), and then allowed to germinate on the ½ MS basal media containing 50 mg/L hygromycin. One day later, the rice seeds from wild-type control lines were placed on the ½ MS basal media without hygromycin and allowed to germinate. Two to three days later, well germinated and consistently grown seeds were transferred to ½ MS basal media and cultivated in an illumination incubator (which simulated natural growth condition of 14-hour light and 10-hour darkness) for 10 days for phenotype observation. More than 30 plants were selected for each of the transgenic and wild-type plant lines, and each experiment was run in triplicate. Results showed that the transgenic plants overexpressing miR164 had obviously larger root systems than the wild-type plants, and had increased numbers of adventitious and lateral roots as well as markedly elongated root hairs (FIG. 5).

Example 5

Figure 6:
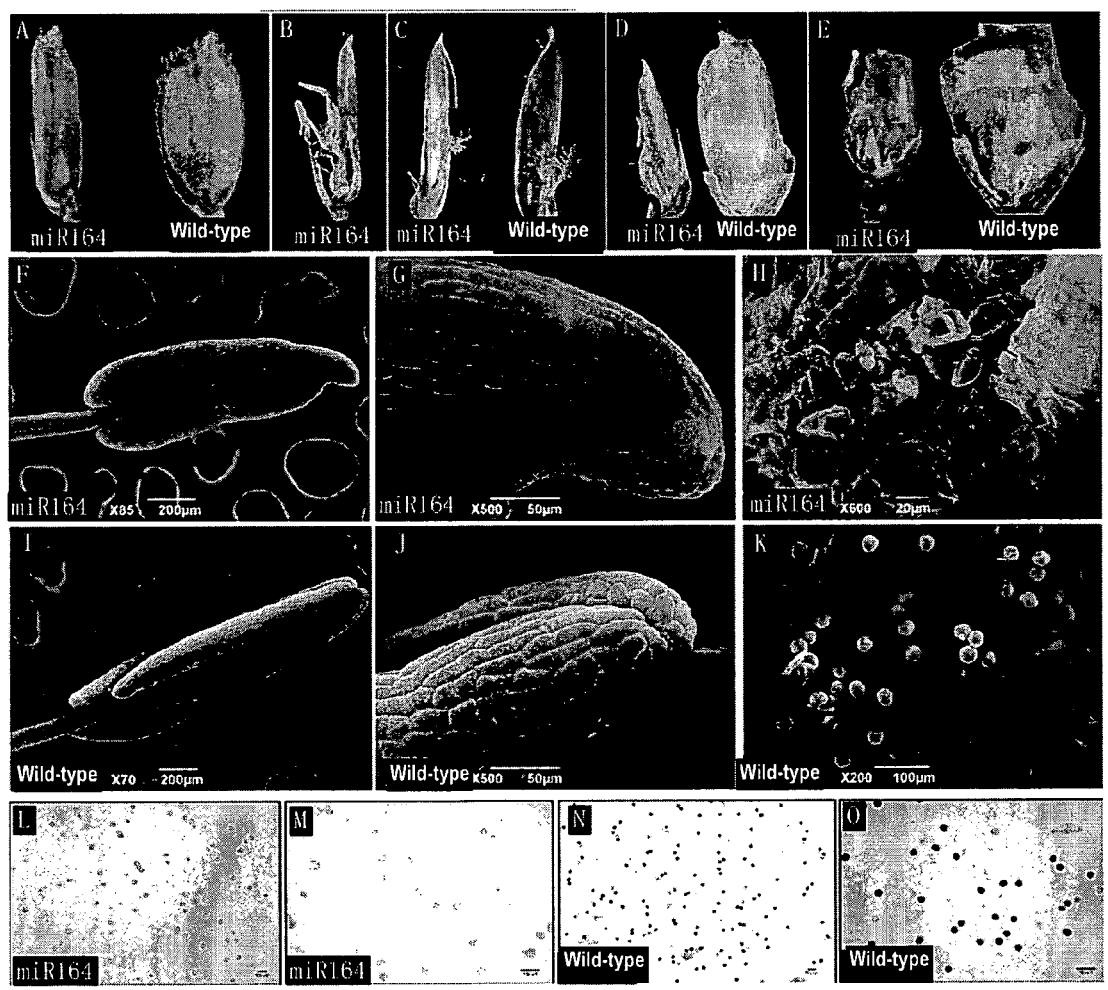
FIG. 6 (including FIG. 6A to FIG. 6O) shows that the transgenic plants overexpressing miR164 are infertile.

Transgenic Plants Overexpressing miR164 were Sterile but their Fertility could be Restored by External Application of Hormones Phenotype observations revealed that the glumes of the transgenic plants overexpressing miR164 became crimpled (FIG. 6A). This abnormality made the glumes unable to open such that the filaments, although elongated, could not extend out of the glumes (FIG. 6B). Anatomy of embryo sacs of the transgenic plants overexpressing miR164 which had flowered showed that endosperms had not been developed, with no endosperms formed in the elongated ovaries after flowering. Moreover, the ovaries of most of the transgenic plants overexpressing miR164 stopped growing or even died (FIG. 6C to 6E). The development of anthers in the transgenic plants overexpressing miR164 was abnormal. SEM observation revealed that the anthers of MI7 before flowering had only two asymmetrical anther sacs, while normal anthers have four anther sacs arranged in a "butterfly" shape. The pollens of the transgenic plants overexpressing miR164 were not in the normal globular shape, but were shrunken (FIG. 6F to 6K). Iodine staining revealed that the pollens of the transgenic plants overexpressing miR164 were completely sterile (FIGS. 6I to 6O). The sterility of the transgenic plants overexpressing miR164 could be utilized to conveniently breed a rice sterile line for hybrid rice breeding.

Figure 7:
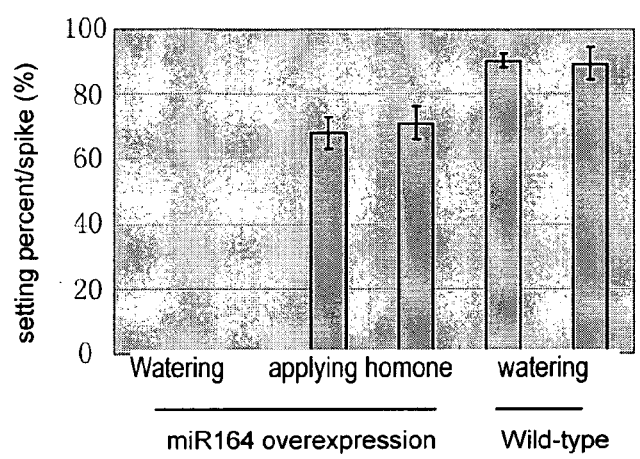
FIG. 7 shows that the fertility phenotype of transgenic plant overexpressing miR164 is restored by application of external hormone. The left panel shows the statistics of the fertility of spikelets, and the right panel shows the overall morphology of a representative plant after becoming mature with or without application of hormones.

Two T0 transgenic plants overexpressing miR164 were continually subjected to external application of four phytohormones, indoleacetic acid (IAA), naphthaleneacetic acid (NAA), kinetin (KT), and 6-benzylaminopurine (6-BA) from tillering stage to grain filling stage, and compared with the transgenic plants overexpressing miR164 grown normally. Results showed that the externally applied hormones rendered the transgenic plants overexpressing miR164 produce seeds normally in the panicles. This indicated that external application of hormones might make up for the defect in development of the transgenic plants overexpressing miR164 so that spikelets and seeds could develop normally when the secondary branches had already been formed (FIG. 7). That the fertility of transgenic rice plants overexpressing miR164 could be restored by external application of hormones can be taken advantage of to conveniently use a transgenic rice plant to breed a sterile line (without application of hormones) or a maintainer line (by external application of hormones to allow the sterile line to produce seeds and to be reproduced; however the next generation is still sterile without externally applied hormones), thereby achieving "the double usage of a single line" for the breeding of hybrid rice.

The invention claimed is:

1. A method of enhancing the root system in a plant, said method comprising:
   (1) overexpressing in a plant a microRNA molecule comprising the RNA nucleotide sequence of SEQ ID NO: 2; and
   (2) selecting a plant from step (1) that has increased numbers of adventitious and lateral roots and elongated root hairs compared to a wild-type plant, wherein said selected plant has an enhanced root system compared to the wild-type plant and is a rice plant.

2. The method of claim 1, wherein said microRNA molecule is produced from a recombinant DNA construct comprising a promoter operably linked to DNA comprising the polynucleotide sequence of SEQ ID NO: 1.

3. The method of claim 2, wherein said promoter is a ubiquitin promoter.

* * * * *

SEQUENCE LISTING

<160> NUMBER OF SEQ ID NOS: 4

<210> SEQ ID NO 1
<211> LENGTH: 887
<212> TYPE: DNA
<213> ORGANISM: Oryza sativa
<220> FEATURE:
<221> NAME/KEY: gene
<222> LOCATION: (1)..(887)

```
<223> OTHER INFORMATION: cDNA
<220> FEATURE:
<221> NAME/KEY: primer_bind
<222> LOCATION: (868)..(887)
<223> OTHER INFORMATION: GPR primer
<220> FEATURE:
<221> NAME/KEY: primer_bind
<222> LOCATION: (1)..(21)
<223> OTHER INFORMATION: GPF primer

<400> SEQUENCE: 1
tggcgacaca gagagagaga ggtagacggt ggccgtgcac ggtggagaag cagggcacgt      60
gcattaccat ccactcgcct gccggccgcc ggccgccatt gccatggatg gttcttcatg     120
tgcccgtctt ctccaccgag caccaactgt ctcgatcggc gtctgaaact ctgaatacat     180
gaattccccc atggccaaaa ccttcctccc aggtttgcat gttgatcaat tttctcctct     240
tctgcttctc caatttcttc ttcgctggag atatcgtagt agtagcattc tttctcaagg     300
gaattccttc tttctcaagg gctgttcttg agagagtgtt ctctctgtga ttaattcttc     360
tagccgattc accggtttcg ccgtcgtttt cgccgcgaaa aaatgtacag gcgagtaggc     420
gaccaccgga atatactggt gattaattag ctgagaactg acgagcaaca ggacactgtt     480
ctaccgtgtg atcatactgt gattgatgca atactgtcgg ttgctgctgc caagctggtt     540
ctgttctctc tcgcacgcaa ttgagcaaat tatattatat tttatttat ttttccttga     600 gatcgatcga ttgtgatggc catgcttgcc accgtgtgct ttctctgctt atcaactgcc     660
tcagtttggg agttattctt cgtccatgtc gccatcaacc agctgacagc aatgcacact     720
gcatataata gttatgaaag gaacaattct agagctgtta ctatcttttt attttctca     780 ttattaattt tagcctatgc accaaaccaa ttctctcaga agatcgaggt aattgcaatt     840
gttaacatta gtgcttatat atatctgtgt ctctccagct cagttcg                   887

<210> SEQ ID NO 2
<211> LENGTH: 21
<212> TYPE: RNA
<213> ORGANISM: Oryza sativa
<220> FEATURE:
<221> NAME/KEY: gene
<222> LOCATION: (1)..(21)
<223> OTHER INFORMATION: microRNA

<400> SEQUENCE: 2
uggagaagca gggcacgugc a                                                21

<210> SEQ ID NO 3
<211> LENGTH: 33
<212> TYPE: DNA
<213> ORGANISM: artificial sequence
<220> FEATURE:
<223> OTHER INFORMATION: synthetic

<400> SEQUENCE: 3
ggtaccaatg gtacctggcg acacagagag aga                                   33

<210> SEQ ID NO 4
<211> LENGTH: 35
<212> TYPE: DNA
<213> ORGANISM: artificial sequence
<220> FEATURE:
<223> OTHER INFORMATION: synthetic

<400> SEQUENCE: 4
ggatccaatg gatcccgaac tgagctggag agaca                                 35
```